(12) United States Patent
Hirose et al.

(10) Patent No.: US 6,670,052 B2
(45) Date of Patent: Dec. 30, 2003

(54) ORGANIC LIGHT EMITTING DIODE

(75) Inventors: Hidekazu Hirose, Minamiashigara (JP); Daisuke Okuda, Minamiashigara (JP); Hirohito Yoneyama, Minamiashigara (JP); Mieko Seki, Minamiashigara (JP); Kiyokazu Mashimo, Minamiashigara (JP); Takeshi Agata, Minamiashigara (JP); Katsuhiro Sato, Minamiashigara (JP)

(73) Assignee: Fuji Xerox Co., Ltd., Tokyo (JP)

( * ) Notice: Subject to any disclaimer, the term of this patent is extended or adjusted under 35 U.S.C. 154(b) by 12 days.

(21) Appl. No.: 09/938,675

(22) Filed: Aug. 27, 2001

(65) Prior Publication Data
US 2002/0050597 A1 May 2, 2002

(30) Foreign Application Priority Data
Aug. 28, 2000 (JP) ........................................ 2000-256801

(51) Int. Cl.[7] .............................. B32B 19/00; B32B 9/00; G03G 15/02; H01L 35/24; H01L 51/00; H01J 1/62; H01J 63/04
(52) U.S. Cl. ...................... 428/690; 428/917; 313/504; 313/506; 257/40; 430/59
(58) Field of Search ................................ 428/690, 917; 528/422, 423; 313/504, 506; 257/40; 430/59

(56) References Cited
U.S. PATENT DOCUMENTS

| | | | | |
|---|---|---|---|---|
| 4,539,507 A | * | 9/1985 | VanSlyke et al. ............ | 313/504 |
| 5,639,581 A | * | 6/1997 | Iwasaki et al. ............... | 430/59 |
| 5,654,119 A | * | 8/1997 | Ishii et al. .................... | 430/9 |
| 5,734,003 A | * | 3/1998 | Iwasaki et al. ............... | 528/89 |
| 5,879,821 A | | 3/1999 | Hsieh | |
| 6,074,791 A | * | 6/2000 | Jennings et al. ............. | 430/58.8 |

FOREIGN PATENT DOCUMENTS

| | | |
|---|---|---|
| JP | 59-194393 A | 11/1989 |
| JP | 11-135262 A | 5/1999 |
| JP | 11135262 * | 5/1999 |
| JP | 11-246660 A | 9/1999 |

OTHER PUBLICATIONS

"Organic Electroluminescent Devices With A Mixed–Layer Structure" by Y. Mori et al., 31p–G–12, Asahi Chemical Industry, Co., Ltd., p. 1086.

(List continued on next page.)

Primary Examiner—Cynthia H. Kelly
Assistant Examiner—C Thompson

(57) ABSTRACT

An organic light emitting diode having high luminous intensity, and providing stabilized performance even during repetitive use and easy to manufacture, by using a charge transporting polymer having the following general formulae (I-1) and (I-2).

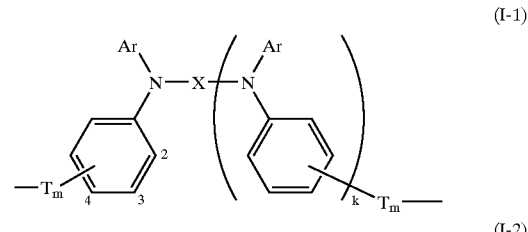

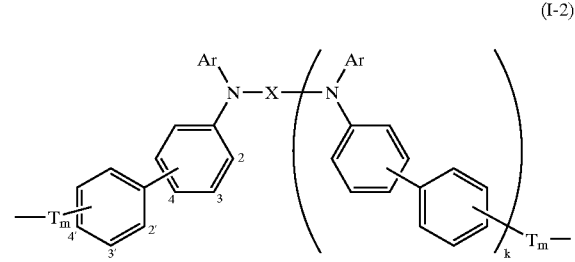

where Ar represents a substituted or non-substituted monovalent polynuclear aromatic ring having number of aromatic rings of 3 to 10, X represents a substituted or non-substituted bivalent aromatic group, T represents a bivalent linear hydrocarbon group of 1 to 6 carbon atoms, m represents an integer of 1 to 3 and k represents 0 or 1.

5 Claims, 1 Drawing Sheet

OTHER PUBLICATIONS

"Flexible Light–Emitting Diodes Made From Soluble Conducting Polymers" by G. Gustafsson et al.; Nature, vol. 357, Jun. 11, 1992, pp. 477–479.

20J–21, Polymer Preprints, Japan, vol. 42, No. 7 (1993) pp. 2860–2863.

"Organic Electroluminescence Devices With A Starburst Amine As A Hole Transport Material" by T. Wakimoto et al., 30a–SZK–14, p. 1146.

"Organic Electroluminenscent Diodes" by C. W. Tang et al., Appl. Phys. Lett. 51 (12), Sep. 21, 1987, pp. 913–915.

"Electrical Conduction and Low Voltage Blue Electroluminescence In Vacuum–Deposited Organic Films" by P.S. Vincett et al., Thin Solid Films, 94 (1982), pp. 171–183, Electronics and Optics.

"Organic EL Device Using Cast Polymer Film As Hole Transport Layer" by T. Fujii et al., 28a–PB–7, p. 1041.

"Preparation Of Organic EL Device By Casting Method" by T. Mori et al., 29p–ZP–5, p. 1006.

* cited by examiner

ORGANIC LIGHT EMITTING DIODE

BACKGROUND OF THE INVENTION

1. Field of the Invention

This invention concerns a device of emitting light by converting an electric energy into light and, more specifically, it relates to an organic light emitting diode which can be used suitably in the field of display devices, backlights, illumination light sources, exposure devices for use in electrophotography, marks and signboards.

2. Description of the Related Art

The light emitting diode is a self light emitting wholly solid device and since it has high visual recognizability and impact strength, a wide applicability is expected.

Those using inorganic fluorescent materials are predominant at present and used generally. However, since they require an AC voltage of 200 volts or higher for driving, they involve a problem of high running cost and insufficient brightness. On the other hand, study for charge light emitting diode using organic compounds has been started initially by using single crystals such as of anthracene. However, the film thickness is as large as about 1 mm and a driving voltage of 100 volts or higher is necessary. Therefore, it has been attempted to reduce the thickness by using a vapor deposition method (Thin Solid Films, 94, (1982) pp.171–183). The phenomenon of light emission of the devices described above is that electrons are injected from one of electrodes and holes are injected from the other of the electrodes to excite the light emitting materiel in the device to a high energy level and the excited luminescence material releases excess energy as a light when they return to the basic state. However, since the driving voltage is still as high as 30 V and the density of electrons hole carriers are low in the film and the probability of generating photons by carrier recombination is low, no sufficient brightness can be obtained and they have not yet been put to practical use.

By the way, Tang, et al. report an organic light emitting diode of a function separation type in which a hole transporting organic low molecular weight compound and a fluorescent organic low molecular weight compound having electron transporting function are laminated successively as extremely thin films by a vacuum vapor deposition method on a transparent substrate, which can provide high brightness of 1000 cd/m$^2$ or more at a low voltage of about 10 V in 1997 (Appl. Phys. Lett., 51 (12), (1987) pp.913–915, and Japanese Published Unexamined Patent Application No. Sho 59-194393) and, from since, vigorous research and development have been conducted for organic charge luminescence devices. The light emitting diode of such lamination structure has a structure in which an organic light emitting material, a charge transporting organic material (charge transporting material) and electrodes are laminated in which holes and electrons move in the charge transporting material and emit light by recombination. As the organic luminescent material, for example, organic dyes emitting fluorescence such as 8-quinolinol aluminum complex or cumarin compounds are used. Further, the charge transporting material can include, for example, N,N-di(m-tollyl)N,N'-diphenyl benzidine or diamino compounds such as 1,1-bis[N,N-di(p-tollyl)aminophenyl] cyclohexane and 4-[N,N-diphenyl) aminobenzaldehyde-N,N-diphenyl hydrozone compound.

However, although the organic light emitting diode has high luminescent characteristics, they involve a problem in the stability upon light emission or store stability. Since the layer formed with the organic material in the light emitting diode is as thin as from several tens to several hundreds namometers, the voltage applied per unit thickness is extremely high and the device is driven at a high current density of several mA/cm$^2$, a great amount of Joule heat is generated. Therefore, it is often observed a phenomenon that the hole transporting low molecular weight compound or the fluorescent organic low molecular compound formed as films by vapor deposition in an amorphous glass state is gradually crystallized and finally melted to lower the brightness or result in dielectric breakdown and, as a result, the life time of the device is lowered. Further, it suffers from aging change and deterioration caused by oxygen-containing atmospheric gas or moisture during long time use.

In view of the above, it has been reported organic light emitting diode of using a star burst amine capable of providing a stable amorphous glass state as the hole transporting material (Extended Abstracts, 40th Annual Meeting of The Japan Society of Applied Physics, 30a-SZK-14 (1993)), or using a polymer formed by introducing a triphenyl amine to the side chain of polyphosphazene (Polymer Preprints, Japan Vol. 42, No. 7 (1993) pp. 2860–2862) for solving the problems in view of the heat stability of light emitting diode. However, since a energy barrier caused by ionizing potential of the hole transporting material is present, they cannot satisfy by themselves the hole chargeability form the anode or the hole chargeability to the light emitting layer. Further, in a case of the former star burst amine, purification is difficult due to the low solubility and it is difficult to enhance the impurity, and the latter polymer cannot provide high current density to obtain a sufficient brightness.

On the other hand, research and development have also been progressed also on the light emitting diode of a single layer structure intending to solve the problems described above and devices using conductive polymers such as poly (p-phenylene vinylene) (Nature Vol. 357 (1992) pp. 477–479) and formed by mixing an electron transporting material and a fluorescent dye in hole transporting polyvinyl carbazole (Extended Abstracts, 38th Annual Meeting of The Japan Society of Applied Physics 31p-G-12 (1991)) have been proposed but they are not still comparable with the laminate type light emitting diode using the organic low molecular weight compound in view of the brightness and the luminous efficacy.

Further, in the preparation method, a coating method is preferred in view of the simplification of manufacture, fabricability, increase of the surface area and it has been reported that devices can be obtained also by a casting method (Extended Abstracts, 50th Annual Meeting of The Japan Society of Applied Physics, 29p-ZP-5 (1989), and the 51st Annual Meeting of The Japan Society of Applied Physics, 28a-PB-7 (1990)). However, since the solubility and compatibility of the charge transporting material to the solvent and the resin are poor, they tend to be crystallized and have drawbacks in view of production or characteristics.

Further, Japanese Published Unexamined Patent Application No. Hei 11-135262 and No. Hei 11-246660 disclose organic electroluminescence material having a triaryl amine or heterocyclic amine structure.

SUMMARY OF THE INVENTION

This invention has been made in view of overcoming the foregoing problems in the related art, and this invention provides an organic light emitting diode having high luminous intensity, providing stable performance even after repeating use and easy to manufacture by using a charge transporting polymer excellent in stability upon light emission, store stability, solubility and compatibility.

The present inventors have made an earnest study on charge transporting polymers for solving the foregoing subject and, as a result, have accomplished this invention, based on the finding that a charge transporting polyether including repeating units containing, as a partial structure, at least one member selected from the structures shown by the following structural formulae (I-1) and (I-2) has a hole charging property, a charge mobility and thin film forming performance, which is suitable as an organic light emitting diode.

According to an aspect of the present invention, an organic light emitting diode has one or more organic compound layers put between a pair of electrodes including an anode and a cathode, one of which is transparent or semi-transparent. At least one of the organic compound layers contains one or more kinds of charge transporting polyethers including a repeating unit containing, as a partial structure, at least one member selected from structures represented by the following general formulae (I-1) and (I-2):

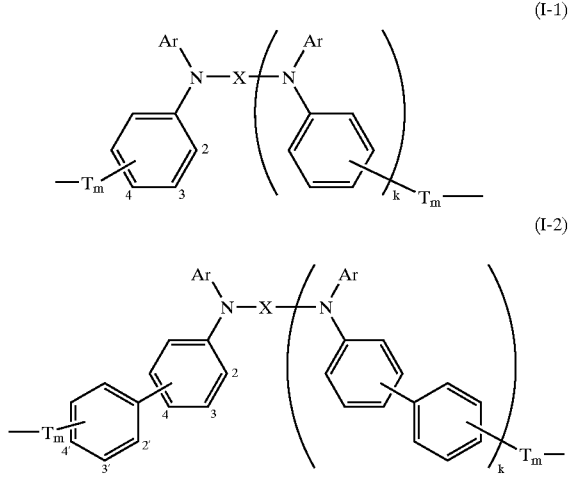

where Ar represents a substituted or non-substituted monovalent polynuclear aromatic ring having a number of aromatic rings of from 3 to 10, or a substituted or non-substituted monovalent condensed aromatic ring having a number of aromatic rings of from 2 to 10, X represents a substituted or non-substituted bivalent aromatic group, T represents a bivalent linear hydrocarbon group of 1 to 6 carbon atoms or a bivalent branched hydrocarbon group of 2 to 10 carbon atoms, m represents an integer of 1 to 3 and k represents 0 or 1.

An organic light emitting diode, according to another aspect of the present invention, has a hole transporting layer containing one or more charge transporting polyethers including repeating units containing, as a partial structure, at least one member selected from structures represented by the general formulae (I-1) and (I-2), and an emitting layer as the organic compound layer in this order on a transparent electrode.

The organic compound layer may be a single layer.

The charge transporting polyether may be a polyether represented by the following general formula (II):

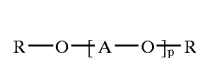

where A represents at least one member of the structures represented by the general formula (I-1) and (I-2), R represents a hydrogen atom, an alkyl group, a substituted or non-substituted aryl group or a substituted or non-substituted aralkyl group and p represents an integer from 5 to 5000.

The organic light emitting diode according to this invention has excellent stability during light emission, store stability and durability. Further, the organic light emitting diode according to this invention can provide an output at high brightness.

BRIEF DESCRIPTION OF THE DRAWINGS

Preferred embodiments of this invention will be described in detail based on the followings, wherein.

DETAILED DESCRIPTION OF THE PREFERRED EMBODIMENTS

Figure 1:
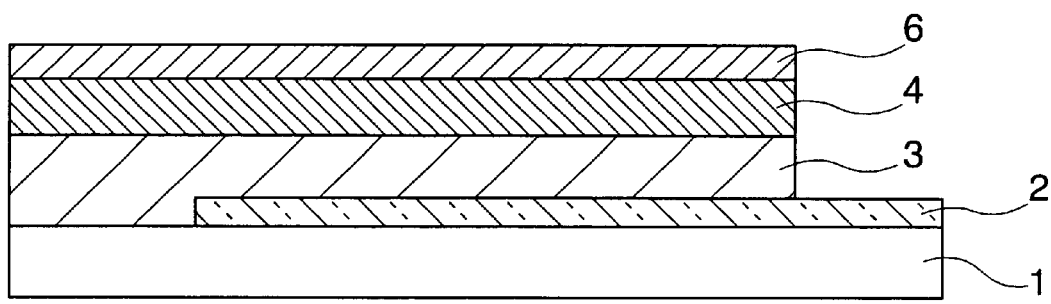
FIG. 1 is a schematic cross sectional view illustrating an example of an organic light emitting diode according to this invention.

Preferred embodiments of the invention are to be explained more specifically.

The organic light emitting diode according to this invention has one or more organic compound layers between a pair of electrodes and, optionally has other layers and materials.

In a case where the organic compound layer includes a single layer, it contains one or more charge transporting polyethers including repeating units containing, as a partial structure, at least one member selected from the structures shown by the general formulae I-1 and I-2 described above in the layer and, in a case where it includes two or more layers, it contains one or more of the charge transporting polyethers in at least one layer.

The organic light emitting diode according to this invention may be either a function separation type, for example, including a hole transporting layer containing a charge transporting polyether including repeating units containing, as a partial structure, at least one member selected from the structures represented by the general formulae I-(1) and I-(2) and an emitting layer in this order on a transparent electrode, or a type having both charge transporting property and light emitting property, that is, having a light emitting layer having a charge transporting property containing a light emitting material in addition to the charge transporting polyether.

The organic compound layer may further contain other charge transporting material (hole transporting material, electron transporting material) other than the charge transporting polyether described above.

The structures represented by the general formulae (I-1) and (I-2) constituting the charge transporting polyether in this invention are to be explained specifically.

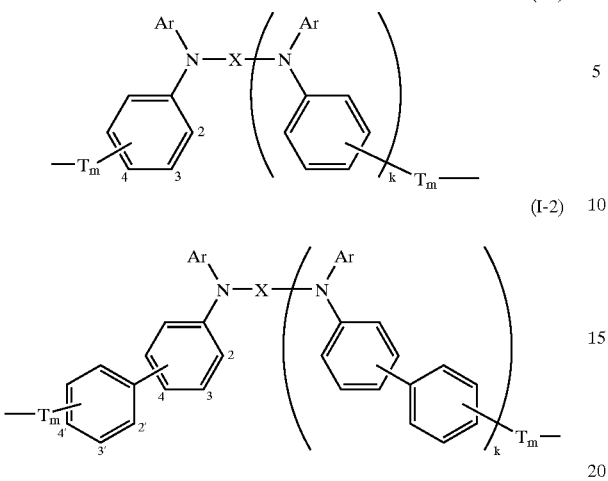

(I-1)

(I-2)

where Ar represents a substituted or non-substituted monovalent polynuclear aromatic ring having a number of aromatic rings of from 3 to 10, or a substituted or non-substituted monovalent condensed aromatic ring having a number of aromatic rings of from 2 to 10, X represents a substituted or non-substituted bivalent aromatic group, T represents a bivalent linear hydrocarbon group of 1 to 6 carbon atoms or a bivalent branched hydrocarbon group of 2 to 10 carbon atoms, m represents an integer of 1 to 3 and k represents 0 or 1).

The substituent for the polynuclear aromatic ring or the condensed aromatic ring represented by Ar can include, for example, a hydrogen atom, an alkyl group, an alkoxy group, an aryl group, an aralkyl group, a substituted amino group, and a halogen atom.

The alkyl group preferably has from 1 to 10 carbon atoms and can include, for example, methyl group, ethyl group, propyl group or isopropyl group. The alkoxy group preferably has 1 to 10 carbon atoms and can include, for example, methoxy group, ethoxy group, propoxy group and isopropoxy group. The aryl group preferably has 6 to 20 carbon atoms and can include, for example, phenyl group and toluyl group. The aralkyl group preferably has 7 to 20 carbon atoms and can include, for example, benzyl group and phenethyl group. The substituent for the substituted amino group can include, for example, alkyl group, aryl group and aralkyl group and the specific examples are as described above.

X represents a substituted or non-substituted bivalent aromatic group and, specifically, can include preferably groups selected from the following formulae (1)–(7).

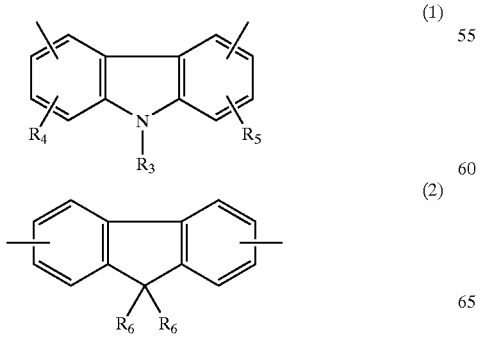

(1)

(2)

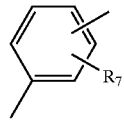

(3)

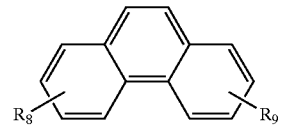

(4)

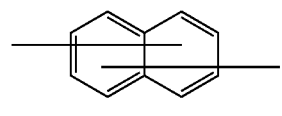

(5)

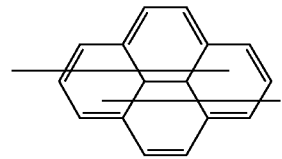

(6)

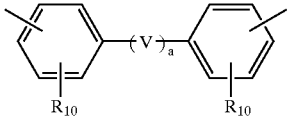

(7)

In the formulae, $R_3$ represents a hydrogen atom, an alkyl group of 1 to 4 carbon atoms, a substituted or non-substituted phenyl group or a substituted or non-substituted aralakyl group, $R_4$-$R_{10}$ each represents independently a hydrogen atom, an alkyl group of 1 to 4 carbon atoms, an alkoxy group of 1 to 4 carbon atoms, a substituted or non-substituted phenyl group, a substituted or non-substituted aralkyl group or a halogen atom, a represents 0 or 1 and V represents the group selected from the following formulae (8)–(17).

—(CH$_2$)$_b$— (8)

—C(CH$_3$)$_2$— (9)

—O— (10)

—S— (11)

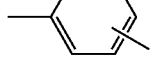 (12)

 (13)

—C(CF$_3$)$_2$— (14)

—Si(CH$_3$)$_2$— (15)

—C≡C— (16)

(17)

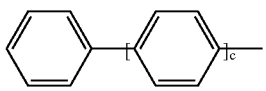

b represents an integer of 1 to 10 and c represents an integer of 1 to 3.

Among all, it is particularly preferred when X has a biphenylene structure represented by the following structural formulae (A) or (B), since a polymer of high mobility can be obtained as reported also in [The Sixth International Congress on Advances in Non-impact Printing Technologies, 306, (1990)].

(A)

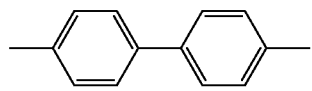

(B)

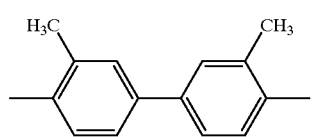

T represents a bivalent linear hydrocarbon group of 1 to 6 carbon atoms or a bivatent branched hydrocarbon group of 2 to 10 carbon atoms, and is selected, preferably, from a bivalent linear hydrocarbon group of 2 to 6 carbon atoms and a bivalent branched hydrocarbon group of 3 to 7 carbon atoms. Preferred specific structures are shown below.

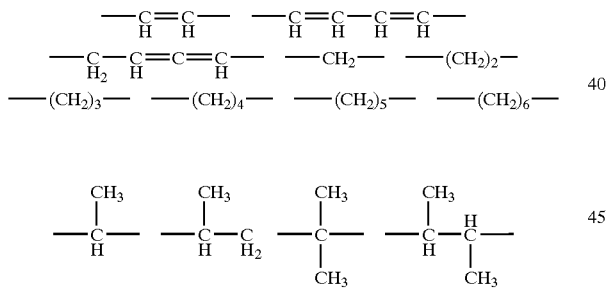

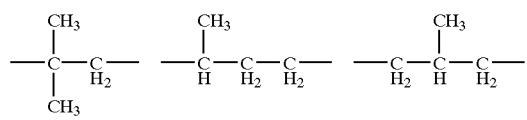

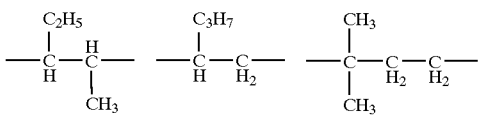

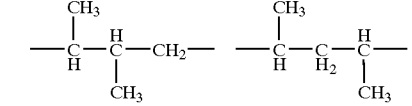

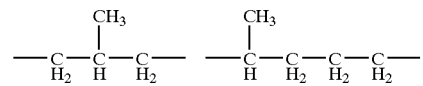

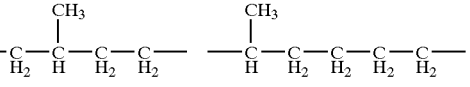

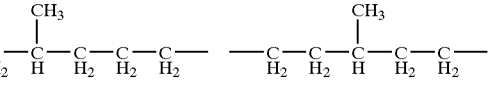

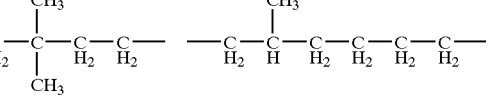

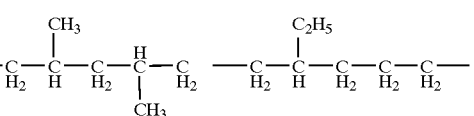

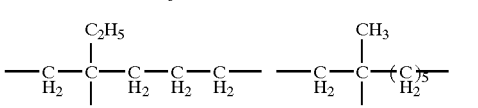

The following Table 1 shows specific examples of the structure represented by the general formula (I-1) and the following Table 2 shows specific examples of the structures represented by the general formula (I-2) but the invention is not restricted to such specific examples.

TABLE 1

| Structure | k | X | Ar | Bonded position | T |
|---|---|---|---|---|---|
| 1. | 0 | 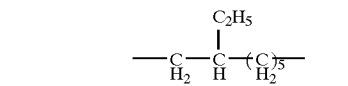 | | 3 | —$CH_2$— |

TABLE 1-continued
| Structure | k | X | Ar | Bonded position | T |
|---|---|---|---|---|---|
| 2. | 0 | 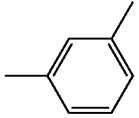 | 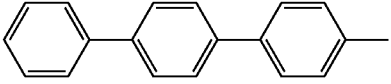 | 3 | —CH$_2$CH$_2$— |
| 3. | 0 | 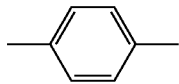 | 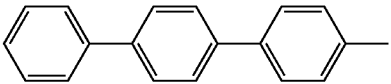 | 3 | —CH$_2$— |
| 4. | 0 | 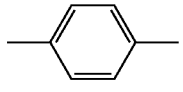 | 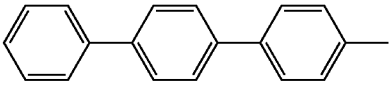 | 3 | —CH$_2$CH$_2$— |
| 5. | 0 | 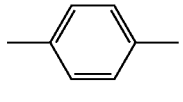 | 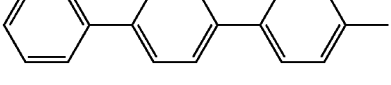 | 4 | —CH$_2$— |
| 6. | 0 | 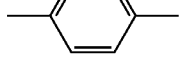 | 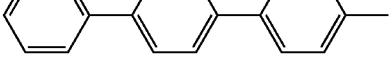 | 4 | —CH$_2$CH$_2$— |
| 7. | 0 | 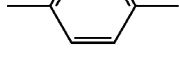 | 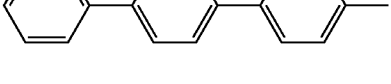 | 4 | 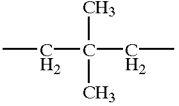 |
| 8. | 0 | 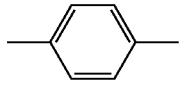 | 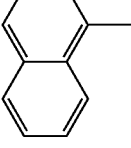 | 4 | —CH$_2$— |
| 9. | 0 | 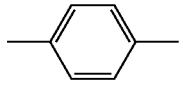 | 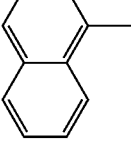 | 4 | —CH$_2$CH$_2$— |
| 10. | 0 | 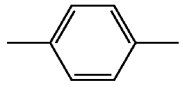 | 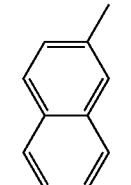 | 4 | —CH$_2$— |
| 11. | 0 | 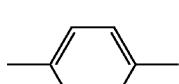 | 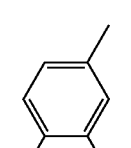 | 4 | —CH$_2$CH$_2$— |

TABLE 1-continued
| Structure | k | X | Ar | Bonded position | T |
|---|---|---|---|---|---|
| 12. | 0 | 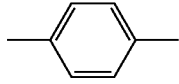 | 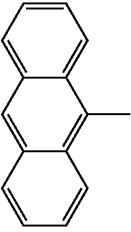 | 4 | —CH$_2$— |
| 13. | 0 | 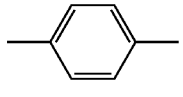 | 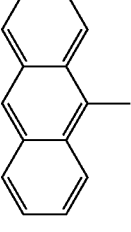 | 4 | —CH$_2$CH$_2$— |
| 14. | 1 | 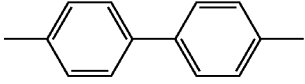 | 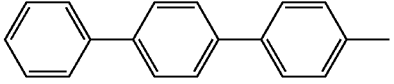 | 2 | —CH$_2$— |
| 15. | 1 | 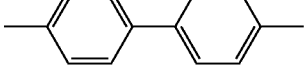 | 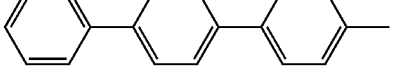 | 3 | —CH$_2$— |
| 16. | 1 | 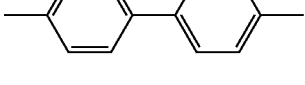 | 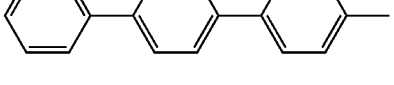 | 4 | —CH$_2$— |
| 17. | 1 | 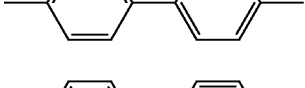 | 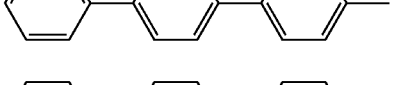 | 2 | —CH$_2$CH$_2$— |
| 18. | 1 | 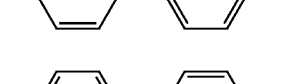 | 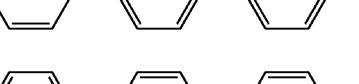 | 3 | —CH$_2$CH$_2$— |
| 19. | 1 |  | 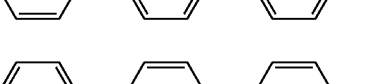 | 4 | —CH$_2$CH$_2$— |
| 20. | 1 |  |  | 3 | —CH$_2$CH$_2$CH$_2$CH$_2$— |
| 21. | 1 | 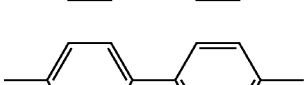 | 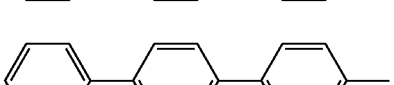 | 4 | —CH$_2$CH$_2$CH$_2$CH$_2$— |
| 22. | 1 |  |  | 4 | 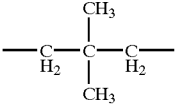 |

TABLE 1-continued
| Structure | k | X | Ar | Bonded position | T |
|---|---|---|---|---|---|
| 23. | 1 | 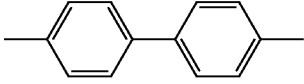 | 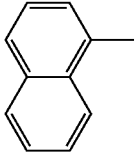 | 3 | —CH$_2$— |
| 24. | 1 | 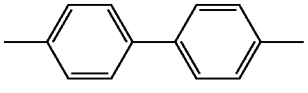 | 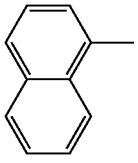 | 4 | —CH$_2$— |
| 25. | 1 | 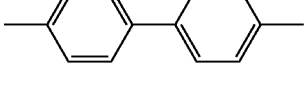 | 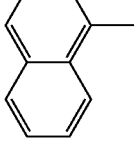 | 3 | —CH$_2$CH$_2$— |
| 26. | 1 | 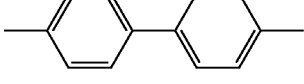 | 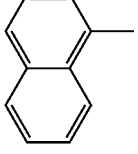 | 4 | —CH$_2$CH$_2$— |
| 27. | 1 | 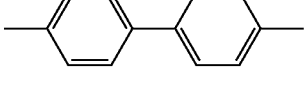 | 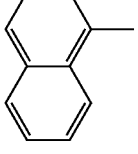 | 3 | —CH$_2$CH$_2$CH$_2$CH$_2$— |
| 28. | 1 | 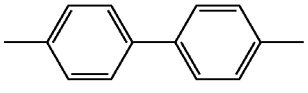 | 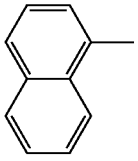 | 4 | —CH$_2$CH$_2$CH$_2$CH$_2$— |
| 29. | 1 | 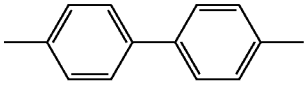 | 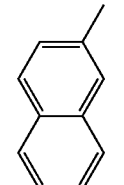 | 3 | —CH$_2$— |
| 30. | 1 | 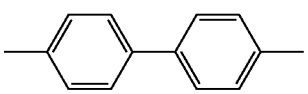 | 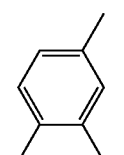 | 4 | —CH$_2$— |

TABLE 1-continued
| Structure | k | X | Ar | Bonded position | T |
|---|---|---|---|---|---|
| 31. | 1 | 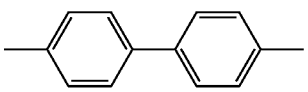 | 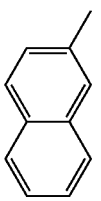 | 3 | —CH$_2$CH$_2$— |
| 32. | 1 | 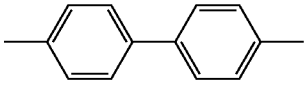 | 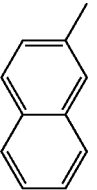 | 4 | —CH$_2$CH$_2$— |
| 33. | 1 | 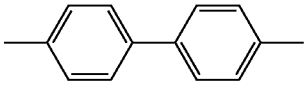 | 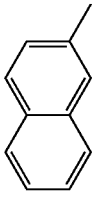 | 3 | —CH$_2$CH$_2$CH$_2$CH$_2$— |
| 34. | 1 | 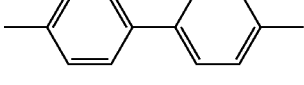 | 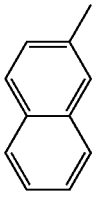 | 4 | —CH$_2$CH$_2$CH$_2$CH$_2$— |
| 35. | 1 | 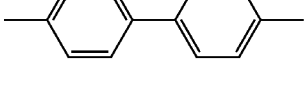 | 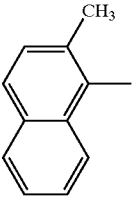 | 4 | —CH$_2$CH$_2$— |
| 36. | 1 | 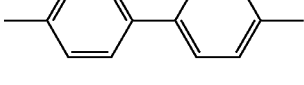 | 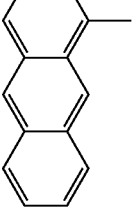 | 4 | —CH$_2$— |
| 37. | 1 | 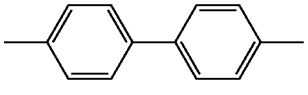 | 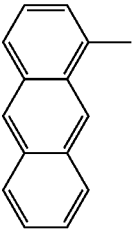 | 4 | —CH$_2$CH$_2$— |

TABLE 1-continued

| Structure | k | X | Ar | Bonded position | T |
|---|---|---|---|---|---|
| 38. | 1 | 3,3'-dimethyl-4,4'-biphenyl | p-terphenyl | 3 | —CH$_2$— |
| 39. | 1 | 3,3'-dimethyl-4,4'-biphenyl | p-terphenyl | 4 | —CH$_2$— |
| 40. | 1 | 3,3'-dimethyl-4,4'-biphenyl | p-terphenyl | 3 | —CH$_2$CH$_2$— |
| 41. | 1 | 3,3'-dimethyl-4,4'-biphenyl | p-terphenyl | 4 | —CH$_2$CH$_2$— |
| 42. | 1 | 3,3'-dimethyl-4,4'-biphenyl | p-terphenyl | 4 | —C(H$_2$)—C(CH$_3$)$_2$—C(H$_2$)— |
| 43. | 1 | 3,3'-dimethyl-4,4'-biphenyl | naphthyl | 3 | —CH$_2$— |
| 44. | 1 | 3,3'-dimethyl-4,4'-biphenyl | naphthyl | 4 | —CH$_2$— |
| 45. | 1 | 3,3'-dimethyl-4,4'-biphenyl | naphthyl | 3 | —CH$_2$CH$_2$— |
| 46. | 1 | 3,3'-dimethyl-4,4'-biphenyl | naphthyl | 4 | —CH$_2$CH$_2$— |

TABLE 1-continued
| Structure | k | X | Ar | Bonded position | T |
|---|---|---|---|---|---|
| 47. | 1 | 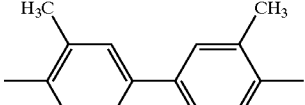 |  | 3 | —CH$_2$— |
| 48. | 1 | 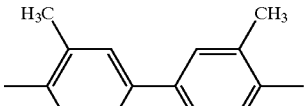 | 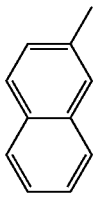 | 4 | —CH$_2$— |
| 49. | 1 | 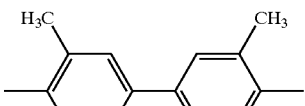 | 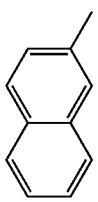 | 3 | —CH$_2$CH$_2$— |
| 50. | 1 | 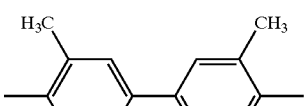 | 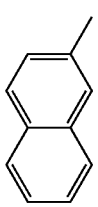 | 4 | —CH$_2$CH$_2$— |
| 51. | 1 | 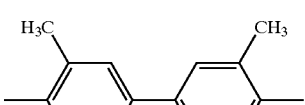 | 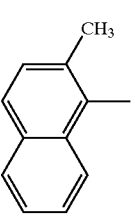 | 4 | —CH$_2$CH$_2$— |
| 52. | 1 | 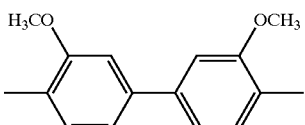 | 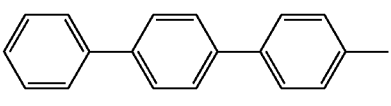 | 4 | —CH$_2$CH$_2$— |
| 53. | 1 |  | 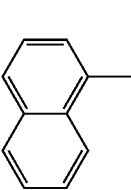 | 4 | —CH$_2$CH$_2$— |
| 54. | 1 | 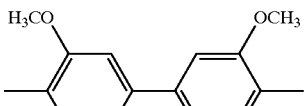 | 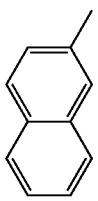 | 4 | —CH$_2$CH$_2$— |

TABLE 1-continued
| Structure | k | X | Ar | Bonded position | T |
|---|---|---|---|---|---|
| 55. | 1 | 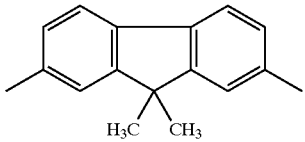 | 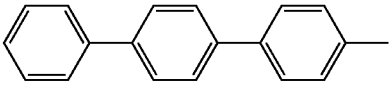 | 4 | —CH$_2$— |
| 56. | 1 | 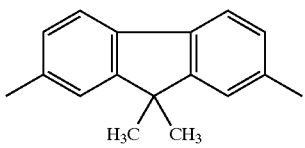 | 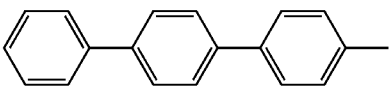 | 4 | —CH$_2$CH$_2$— |
| 57. | 1 | 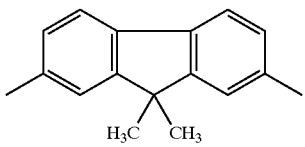 | 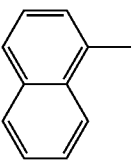 | 4 | —CH$_2$CH$_2$— |
| 58. | 1 | 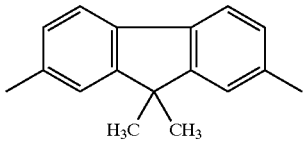 | 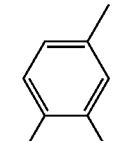 | 4 | —CH$_2$CH$_2$— |
| 59. | 1 | 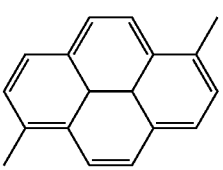 | 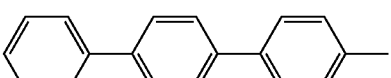 | 4 | —CH$_2$CH$_2$— |
TABLE 2
| Structure | k | X | Ar | Bonded position | T |
|---|---|---|---|---|---|
| 60. | 0 | 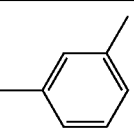 | 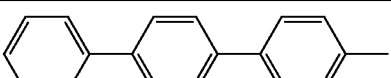 | 4,4' | —CH$_2$— |
| 61. | 0 | 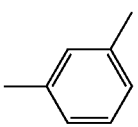 | 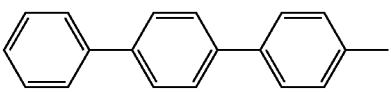 | 4,4' | —CH$_2$CH$_2$— |
| 62. | 0 | 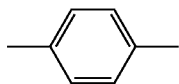 | 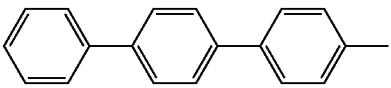 | 4,4' | —CH$_2$— |
| 63. | 0 | 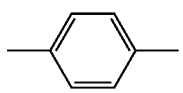 | 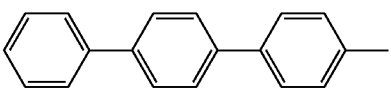 | 4,4' | —CH$_2$CH$_2$— |

TABLE 2-continued

| Structure | k | X | Ar | Bonded position | T |
|---|---|---|---|---|---|
| 64. | 0 | *p-phenylene* | *4-biphenylyl-phenylene* | 4,4' | $-\text{CH}_2-\text{C}(\text{CH}_3)_2-\text{CH}_2-$ |
| 65. | 0 | *p-phenylene* | *1-naphthylene* | 4,4' | $-\text{CH}_2-$ |
| 66. | 0 | *p-phenylene* | *1-naphthylene* | 4,4' | $-\text{CH}_2\text{CH}_2-$ |
| 67. | 0 | *p-phenylene* | *1-naphthylene* | 4,4' | $-\text{CH}_2-$ |
| 68. | 0 | *p-phenylene* | *2-naphthylene* | 4,4' | $-\text{CH}_2\text{CH}_2-$ |
| 69. | 0 | *p-phenylene* | *9-anthracenyl* | 4,4' | $-\text{CH}_2-$ |
| 70. | 0 | *p-phenylene* | *9-anthracenyl* | 4,4' | $-\text{CH}_2\text{CH}_2-$ |
| 71. | 1 | *biphenylene* | *terphenylene* | 4,4' | $-\text{CH}_2-$ |
| 72. | 1 | *biphenylene* | *terphenylene* | 4,4' | $-\text{CH}_2\text{CH}_2-$ |

TABLE 2-continued
| Structure | k | X | Ar | Bonded position | T |
|---|---|---|---|---|---|
| 73. | 1 | 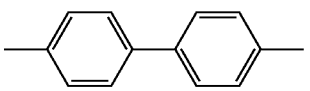 | 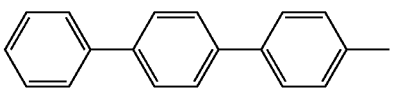 | 4,4' | —CH₂CH₂CH₂CH₂— |
| 74. | 1 | 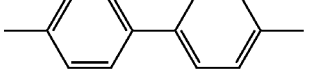 | 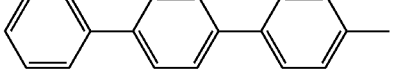 | 4,4' | 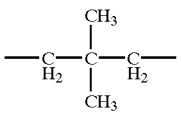 |
| 75. | 1 | 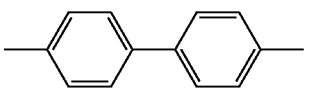 | 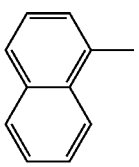 | 4,4' | —CH₂— |
| 76. | 1 | 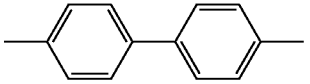 | 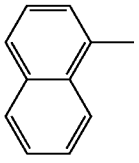 | 4,4' | —CH₂CH₂— |
| 77. | 1 | 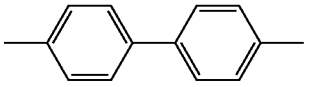 | 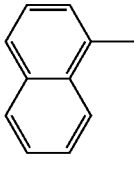 | 4,4' | —CH₂CH₂CH₂CH₂— |
| 78. | 1 | 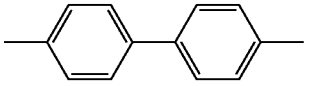 | 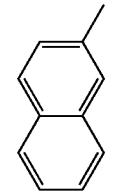 | 4,4' | —CH₂— |
| 79. | 1 | 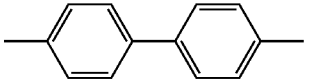 | 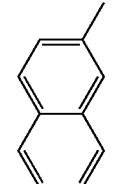 | 4,4' | —CH₂CH₂— |
| 80. | 1 | 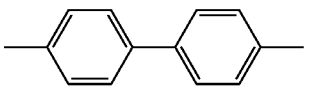 | 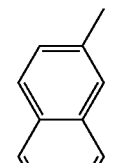 | 4,4' | —CH₂CH₂CH₂CH₂— |

TABLE 2-continued
| Structure | k | X | Ar | Bonded position | T |
|---|---|---|---|---|---|
| 81. | 1 | 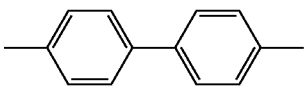 | 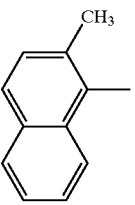 | 4,4' | —CH$_2$CH$_2$— |
| 82. | 1 | 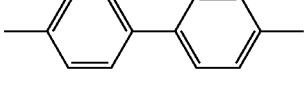 | 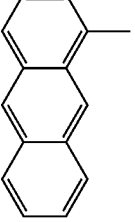 | 4,4' | —CH$_2$— |
| 83. | 1 | 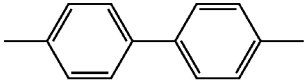 | 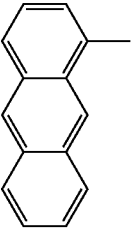 | 4,4' | —CH$_2$CH$_2$— |
| 84. | 1 | 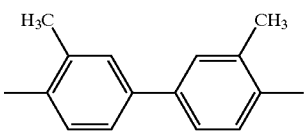 | 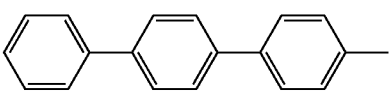 | 4,4' | —CH$_2$— |
| 85. | 1 | 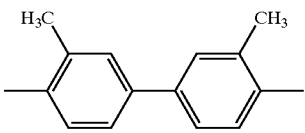 | 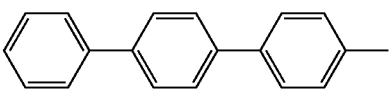 | 4,4' | —CH$_2$CH$_2$— |
| 86. | 1 | 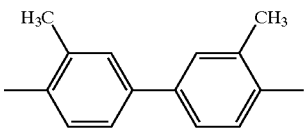 | 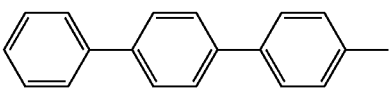 | 4,4' | 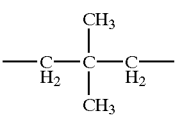 |
| 87. | 1 | 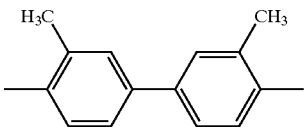 | 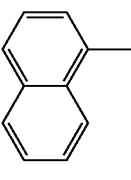 | 4,4' | —CH$_2$— |
| 88. | 1 | 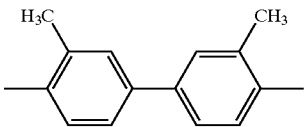 | 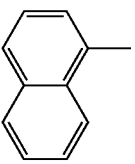 | 4,4' | —CH$_2$CH$_2$— |

TABLE 2-continued

| Structure | k | X | Ar | Bonded position | T |
|---|---|---|---|---|---|
| 89. | 1 | 3,3'-dimethyl-4,4'-biphenylene | 2-naphthyl | 4,4' | —CH$_2$— |
| 90. | 1 | 3,3'-dimethyl-4,4'-biphenylene | 2-naphthyl | 4,4' | —CH$_2$CH$_2$— |
| 91. | 1 | 3,3'-dimethyl-4,4'-biphenylene | 2-methyl-1-naphthyl | 4,4' | —CH$_2$CH$_2$— |
| 92. | 1 | 3,3'-dimethoxy-4,4'-biphenylene | p-terphenyl | 4,4' | —CH$_2$CH$_2$— |
| 93. | 1 | 3,3'-dimethoxy-4,4'-biphenylene | 1-naphthyl | 4,4' | —CH$_2$CH$_2$— |
| 94. | 1 | 3,3'-dimethoxy-4,4'-biphenylene | 2-naphthyl | 4,4' | —CH$_2$CH$_2$— |
| 95. | 1 | 9,9-dimethyl-2,7-fluorenylene | p-terphenyl | 4,4' | —CH$_2$— |
| 96. | 1 | 9,9-dimethyl-2,7-fluorenylene | p-terphenyl | 4,4' | —CH$_2$CH$_2$— |

TABLE 2-continued

| Structure | k | X | Ar | Bonded position | T |
|---|---|---|---|---|---|
| 97. | 1 | 2,7-dimethyl-9,9-dimethylfluorene | 1-naphthyl | 4,4' | —CH$_2$CH$_2$— |
| 98. | 1 | 2,7-dimethyl-9,9-dimethylfluorene | 2-naphthyl | 4,4' | —CH$_2$CH$_2$— |
| 99. | 1 | 1,6-dimethylpyrene | p-terphenyl | 4,4' | —CH$_2$CH$_2$— |

As the charge transporting polyether including the repeating unit containing, as a partial structure, at least one member selected from the structures represented by the general formulae (I-1) and (I-2), those represented by the following general formula (II) are used suitably.

(II)

In the general formula (II), A represents at least one of the structures represented by the general formulae (I-1) and (I-2), which may contain two or more kinds of structures A in one polymer. R represents a hydrogen atom, an alkyl group, a substituted or non-substituted aryl group or a substituted or non-substituted aralkyl group. The alkyl group preferably has 1 to 10 carbon atoms and can include, for example, methyl group, ethyl group, propyl group and isopropyl group. The aryl group preferably has 6 to 20 carbon atoms and can include, for example, phenyl group and toluyl group. The aralkyl group preferably has 7 to 20 carbon atoms and can include, for example, benzyl group and phenethyl group. Further, the substituent for the substituted aryl group or the substituted aralkyl group can include, for example, a hydrogen atom, an alkyl group, an alkoxy group, substituted amino group and a halogen atom.

In general formula (II), p represents an integer of 5 to 5,000. The charge transporting polyether used in this invention, preferably, has an average weight molecular weight Mw within a range from 10,000 to 300,000.

The following Table 3 shows specific examples of the charge transporting polyethers represented by the general formula (II) but the invention is not restricted to such specific examples. In Table 3, numbers for the monomer represent the numbers for the structures represented by the general formula (I-1) or (I-2) shown in Table 1 and Table 2 and m means m in the general formulae (I-1) and (I-2).

TABLE 3

| Compound | Monomer Monomer | Monomer Ratio | M | p |
|---|---|---|---|---|
| (1) | 1 | — | 1 | 90 |
| (2) | 2 | — | 1 | 100 |
| (3) | 4 | — | 1 | 135 |
| (4) | 4 | — | 1 | 45 |
| (5) | 4 | — | 2 | 30 |
| (6) | 4 | — | 1 | 60 |
| (7) | 4 | — | 1 | 35 |
| (8) | 4 | — | 1 | 15 |
| (9) | 4 | — | 1 | 15 |
| (10) | 5 | — | 1 | 155 |
| (11) | 5 | — | 2 | 50 |
| (12) | 6 | — | 1 | 150 |
| (13) | 7 | — | 1 | 30 |
| (14) | 8 | — | 2 | 25 |
| (15) | 9 | — | 1 | 120 |
| (16) | 10 | — | 1 | 150 |
| (17) | 10 | — | 1 | 15 |
| (18) | 10 | — | 1 | 20 |
| (19) | 10 | — | 1 | 20 |
| (20) | 10 | — | 1 | 20 |
| (21) | 11 | — | 1 | 160 |
| (22) | 12 | — | 1 | 25 |
| (23) | 13 | — | 1 | 40 |
| (24) | 14 | — | 1 | 25 |
| (25) | 15 | — | 1 | 25 |
| (26) | 16 | — | 1 | 150 |
| (27) | 22 | — | 1 | 140 |
| (28) | 22 | — | 1 | 30 |
| (29) | 22 | — | 1 | 20 |
| (30) | 22 | — | 1 | 25 |
| (31) | 23 | — | 1 | 20 |
| (32) | 23 | — | 1 | 160 |
| (33) | 23 | — | 1 | 20 |
| (34) | 39 | — | 1 | 15 |
| (35) | 4 | — | 1 | 165 |
| (36) | 31 | — | 1 | 115 |
| (37) | 17 | — | 1 | 180 |
| (38) | 19 | — | 1 | 55 |
| (39) | 21 | — | 1 | 45 |

TABLE 3-continued

| Compound | Monomer | Ratio | M | p |
|---|---|---|---|---|
| (40) | 4/1 | 1/1 | 1 | 130 |
| (41) | 4/13 | 1/1 | 1 | 155 |
| (42) | 4/13 | 1/1 | 1 | 160 |
| (43) | 4/13 | 1/1 | 1 | 20 |
| (44) | 4/31 | 1/1 | 1 | 110 |
| (45) | 4/31 | 1/1 | 2 | 115 |
| (46) | 4/33 | 1/1 | 1 | 125 |
| (47) | 4/8/31 | 1/1/1 | 1 | 170 |
| (48) | 8/31 | 1/1 | 1 | 110 |
| (49) | 8/31 | 1/1 | 1 | 20 |
| (50) | 8/31 | 1/2 | 1 | 95 |
| (51) | 8/31 | 2/1 | 1 | 115 |

The charge transporting polyether including repeating units containing, as a partial structure, at least one member selected from the structures represented by the general formulae (I-1) and (I-2) can be prepared easily by intramolecular condensation of charge transporting compounds having hydroxyl groups represented by the following general formulae (III-1) and (III-2):

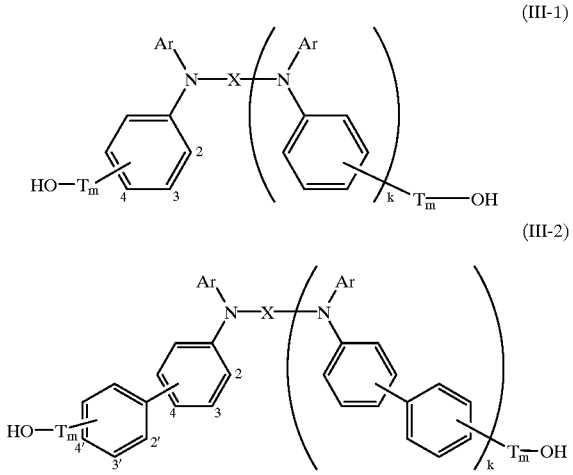

In the formulae (III-1) and (III-2), Ar, X, T, m, k have the same meanings as Ar, X, T, m and k, respectively, in the general formulae (I-1) and (I-2).

The charge transporting polymer can be synthesized, for example, as described below.

(1) The charge transporting polyether can be synthesized by a method of heat-condensing under dehydration the charge transporting compound having two hydroxy alkyl groups (charge transporting monomers) among those represented by the general formulae (III-1) and/or (III-2). In this case, the charge transporting monomers are heat melted with no solvent to conduct polymerizing reaction under dewatering. In this case, it is desirable to react them at a reduced pressure in order to promote the polymerizing reaction by dehydration. Further, in a case of using the solvent, a solvent azeotropically boiling with water, for example, trichloroethane, toluene, chlorobenzene, dichlorobenzene, nitrobenzene or 1-chloronaphthalene is effective for removing water and the solvent is used within a range from 1 to 100 equivalent amount, preferably, from 2 to 50 equivalent amount per one equivalent amount of the charge transporting monomer. The reaction temperature can be set optionally and it is preferred to react them at the boiling point of the solvent in order to remove water that is formed during polymerization. If the polymerization does not proceed, the solvent may be removed from the reaction system and the system may be stirred while heating in a viscous state.

(2) The charge transporting polyether can be synthesized also by a dehydrating condensing method of using a protonic acid such as a p-toluene sulfonic acid, hydrochloric acid, sulfuric acid and trifluoroacetic acid or a Lewis acid such as zinc chloride as the acid catalyst. In this case, the acid catalyst is used within a range from $1/10000$ to $1/10$ equivalent amount, preferably, from $1/1000$ to $1/50$ equivalent amount per one equivalent amount of the charge transporting monomer. A solvent capable of azeotropically boiling with water is used preferably for removing water that is formed during polymerization. As the solvent, toluene, chlorobenzene, dichlorobenzene, nitrobenzene or 1-chloronaphthalene is effective and it is used within a range from 1 to 100 equivalent amount, preferably, from 2 to 50 equivalent amount per one equivalent amount of the charge transporting monomer. The reaction temperature can be set optionally and it is preferred to react them at the boiling point of the solvent in order to remove water that is formed during polymerization.

(3) The charge transporting polyether can be synthesized also by a method of using a condensing agent, for example, an alkyl isocyanate such as cyclohexyl isocyanate, alkyl isocyanate such as cyclohexyl cyanate, cyanate ester such as p-tollyl cyanate and 2,2-bis(4-cyanate phenyl) propane, dichlorohexyl carbodiimide (DCC) or trichloroacetonitrile. In this case, the condensing agent is used within a range from ½ to 10 equivalent amount, preferably, 1 to 3 equivalent amount per one equivalent amount of the charge transporting monomer. As the solvent, toluene, chlorobenzene, dichlorobenzene, or 1-chloronaphthalene is effective and it is used within a range from 1 to 100 equivalent amount, preferably, from 2 to 50 equivalent amount per one equivalent amount of the charge transporting monomer. The reaction temperature can be set optionally and it is preferred to react them at a temperature from the room temperature to the boiling point of the solvent. Among the synthesis method (1), (2) and (3) described above, the synthesis methods (1) and (3) are preferred since isomerization and side reaction less occur. Particularly, the synthesis method (3) is preferred since the reaction conditions are more moderate.

After the completion of the reaction, the reaction product is dissolved into a solvent capable of dissolving the same in a case of not using the solvent for the reaction. In a case of using the solvent, the reaction product is dropped as it is in a poor solvent such as alcohols, for example, methanol or ethanol or acetone to which the charge transporting polyether is less soluble, the charge transporting polyether is precipitated and the charge transporting polyether is separated and then thoroughly washed with water or an organic solvent and dried.

Further, if necessary, re-precipitation treatment of dissolving the product into an appropriate organic solvent and dropping them into a poor solvent to precipitate the charge transporting polyether may be repeated. The re-precipitation treatment is conducted preferably while stirring efficiently by using a mechanical stirrer or the like. The solvent for dissolving the charge transporting polyether in the re-precipitation treatment is used within a range from 1 to 100 equivalent, preferably, from 2 to 50 equivalent amount per one equivalent amount of the charge transporting polyether. Further, the poor solvent is used within a range from 1 to 1000 equivalent amount, preferably, 10 to 500 equivalent amount based on one equivalent amount of the charge transporting polyether. Further, a copolymer can also be synthesized by using 2 or more, preferably 2 to 5 and, further preferably, 2 to 3 kinds of the charge transporting monomers in the reaction described above. Electrical property, film forming property and solubility can be controlled by copolymerizing different kinds of charge transporting monomers.

The degree of polymerization of the charge transporting polyether is set within a range from 5 to 5000, preferably, 10 to 3000, more preferably, 15 to 1000 since the film forming property is poor and no strong film can be obtained easily if the degree is excessively low, whereas solubility to the solvent is lowered to worsen the fabricability if the degree is excessively high.

The terminal group of the charge transporting polyether may be a hydroxyl group like the charge transporting monomer, that is, R in the general formula (II) may be a hydrogen atom. When this gives an effect on the polymer physical property such as solubility, film forming property and mobility, the physical property can be controlled by modifying the terminal group R. For example, the terminal hydroxyl group may be alkyl etherified with an alkyl sulfate or alkyl iodide. The specific reagent can be selected, for example, from dimethyl sulfate, diethyl sulfate, methyl iodide and ethyl iodide and is used within a range from 1 to 3 equivalent amount, preferably, 1 to 2 equivalent amount based on one terminal hydroxyl group. In this case, a basic catalyst can be used and the basic catalyst can be selected optionally, for example, from sodium hydroxide, potassium hydroxide, sodium hydride and sodium metal, which is used within a range to 3 equivalent amount, preferably, from 1 to 2 equivalent amount based on one terminal hydroxyl group. The reaction can be conducted at a temperature from 0° C. to the boiling point of the solvent used.

Further, as the solvent for the reaction, a solvent selected from inert solvents such as benzene, toluene, methylene chloride, tetrahydrofuran, N,N-dimethylformamide, dimethyl sulfoxide, N-methyl pyrrolidone or 1,3-dimethyl-2-imidazolidinone can be used alone or as a mixed solvent including 2 to 3 kinds of solvents. Depending on the reaction, a quaternary ammonium salt such as tetra-n-butyl ammonium iodide can also be used as a phase transfer catalyst. Further, the terminal hydroxyl group can be acylated by using an acid halide to convert the group R into an acyl group. The acyl halide has no particular restriction and can include, for example, acryloyl chloride, crotonoyl chloride, methacryloyl chloride, n-buthyl chloride, 2-furoyl chloride, benzoyl chloride, cyclohexanecarbonyl chloride, enanthyl chloride, phenylacetyl chloride, o-toluoyl chloride, m-toluoyl chloride, and p-toluoyl chloride, which is used within a range from 1 to 3 equivalent amount, preferably, from 1 to 2 equivalent amount based on one terminal hydroxyl group.

In this case, the basic acid can be used and the basic acid can be selected optionally from pyridine, dimethylaminopyridine, trimethyl amine and triethyl amine, which is used within a range from 1 to 3 equivalent amount, preferably, from 1 to 2 equivalent amount based on the acid chloride. The solvent used for the reaction can include, for example, benzene, toluene, methylene chloride, tetrahydrofuran and methyl ethyl ketone. The reaction can be conducted at a temperature from 0° C. to the boiling point of the solvent. Further, acylation can be conducted also by using an acid anhydride such as acetic anhydride. When a solvent is used, an inert solvent such as benzene, toluene or chlorobenzene can be used specifically. The reaction can be conducted at a temperature from 0° C. to the boiling point of the solvent.

In addition, a urethane residue (—CONH—R') can be introduced to the terminal end by using a monoisocyanate. Specific monoisocyanate can be selected optionally, for example, from benzyl isocyanate, n-butyl isocyanate, t-butyl isocyanate, cyclohexyl isocyanate, 2,6-dimethyl isocyanate, ethyl isocyanate, isopropyl isocyanate, 2-methoxyphenyl isocyanate, 4-methoxyphenyl isocyanate, n-octadecyl isocyanate, phenyl isocyanate, 1-propyl isocyanate, m-tolyl isocyanate, p-tolyl isocyanate, and 1-naphtyl isocyanate, which is used within a range from 1 to 3 equivalent amount, preferably, 1 to 2 equivalent amount per one the terminal hydroxyl group.

The solvent used for the reaction can include, for example, benzene, toluene, chlorobenzene, dichlorobenzene, methylene chloride, tetrahydrofuran, N,N-dimethylformamide, dimethylsulfoxide, N-methylpyrrolidone, and 1,3-dimethyl-2-imidazolidinone. The reaction can be conducted at a temperature from 0° C. to the boiling point of the solvent used. If the reaction less proceeds, a metal compound such as dibutyl tin (II) dilaurate, tin (II) octylate and lead naphthenate, or tertiary amine such as triethylamine, trimethylamine, pyridine and dimethyl amino pyridine can be added as the catalyst.

Then, explanation is to be made to the layer constitution of the organic compound layer and a pair of electrodes in the organic light emitting diode according to this invention. In this invention, when one organic compound layer is used, this organic compound layer means an emitting layer. Further, if plural organic compound layers are used, this means that one of them is an emitting layer and other organic compound layers include a hole transporting layer, an electron transporting layer, or a hole transporting layer and an electron transporting layer.

Figure 2:
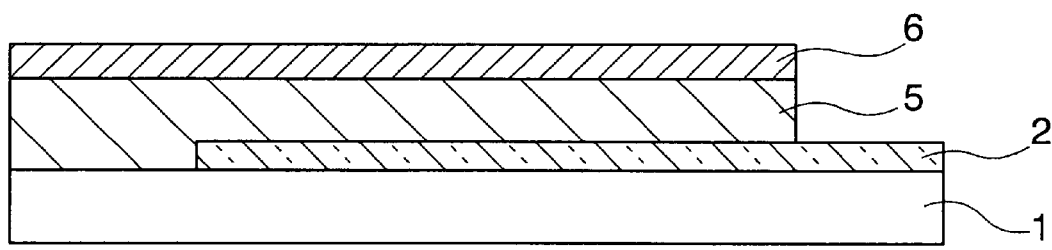
FIG. 2 is a schematic cross sectional view illustrating another example of an organic light emitting diode according to this invention.

FIG. 1 and FIG. 2 are schematic cross sectional views for explaining examples of the layer constitution of organic light emitting diode according to this invention. This invention is not restricted to such layer constitutions. FIG. 1 is an example of using plural organic compound layers, in which a transparent electrode 2, a hole transporting layer 3, an emitting layer 4 and a back electrode 6 are formed in this order on a transparent insulator substrate 1. FIG. 2 is an example of using one organic compound layer, in which a transparent electrode 2, an emitting layer 5 having a charge transporting property and back electrode 6 are disposed in this order on a transparent insulator substrate 1. There is no particular restriction on the electrodes used in this invention so long as they are a pair of electrodes including an anode and a cathode and at least one of them is transparent or semitransparent.

The transparent insulator substrate 1 in FIG. 1 and FIG. 2 is preferably transparent for taking out emission of light, for which a glass or plastic film is used. "Transparent" means that the transmittance for the light in the visible region is 10% or more and, preferably, 75% or higher.

The transparent electrode 2 in FIG. 1 and FIG. 2 is preferably transparent for taking out luminescence like the transparent insulative substrate and preferably has a large work function for injecting holes and those with a work function of 4 eV or more are preferred. Specifically, oxide films such as of tin indium oxide (ITO), tin oxide (NESA), indium oxide and zinc oxide, as well as vapor deposited or sputtered gold, platinum or palladium are used. The electrode, preferably, has a sheet resistance as low as possible, with the resistance of several hundreds Ω/□ or less being preferred. Further, like the transparent insulative substrate, the transmittance of light in the visible region is preferably 10% or more and, further preferably, 75% or more.

The organic compound layer containing at least one kind of the charge transporting polyether including repeating units containing, as a partial structure, at least one member selected from the structures represented by the general formulae (I-1) and (I-2) is the hole transporting layer 3 in the layer constitution of the organic light emitting diode shown in FIG. 1 and the emitting layer 5 having the charge transporting property in the layer constitution of the organic light emitting diode shown in FIG. 2. The emitting layer 4 in FIG. 1 may contain the charge transporting polyether as well.

In the layer constitution of the organic light emitting diode shown in FIG. 1, the hole transporting layer 3 may be formed solely of the charge transporting polyether but may be formed by mixing a tetraphenylene diamine derivative within a range from 1% to 50% by weight for controlling the hole mobility. Further, an appropriate resin (polymer) or additive may also be added in order to improve the film forming property and prevent pin holes.

Specific resin usable for this purpose can include, for example, polycarbonate resin, polyester resin, methacryl resin, acryl resin, polyvinyl chloride resin, cellulose resin, urethane resin, epoxy resin, polystyrene resin, polyvinyl acetate resin, styrene-butadiene copolymer, vinylidene chloride-acrylonitrile copolymer, vinyl chloride-vinyl acetate-maleic anhydride copolymer, silicon resin, poly-N-vinylcarbazol resin, polysilane resin, and conductive resin such as polythiopnene and polypyrrole. Further, as additives, known antioxidants, UV-absorbents and plasticizers can be used.

For the emitting layer 4 in FIG. 1, a compound showing high fluorescent quantum yield in a solid sate is used as the luminescent material. Further, as has been described above, the emitting layer 4 may contain the charge transporting polyether.

When the luminescent material is an organic low molecular weight material, it is a necessary condition that a favorable thin film can be formed by a vacuum vapor deposition method or by coating and drying a solution or liquid dispersion containing the low molecular weight material and the resin. The resin used herein, those exemplified above for the hole transporting layer can be applied. Further, when the luminescent material is a high molecular weight material, it is a necessary condition that a favorable thin film can be formed by coating and drying the solution or the liquid dispersion containing the material itself.

Preferably, for the organic low molecular weight material, chelate type organic metal complexes, polynuclear or fused aromatic ring compounds, perylene derivatives, cumarine derivatives, styrylarylene derivatives, silole derivatives, oxazole derivatives, oxathiazole derivatives, and oxadiazole derivatives can be used. For high molecular weight material, polyparaphenylene derivatives, polyparaphenylenevinylene derivatives, polythiophene derivatives, polyacetylene derivatives and the like can be used.

Preferred specific examples of the luminescent materials can include the following compounds (IV-1) to (IV-15), with no particular restriction to them.

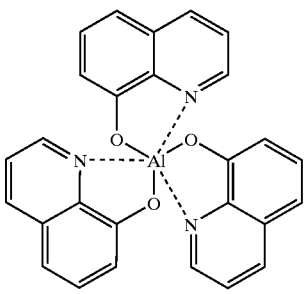
(IV-1)

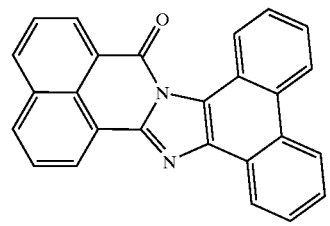
(IV-2)

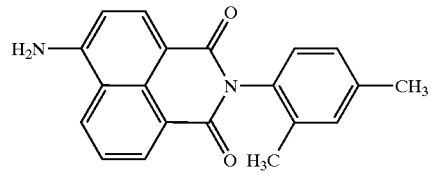
(IV-3)

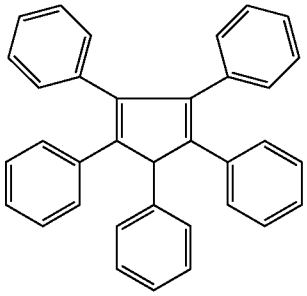
(IV-4)

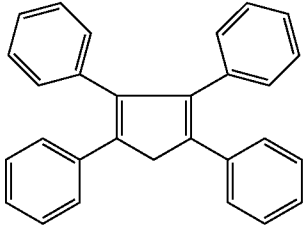
(IV-5)

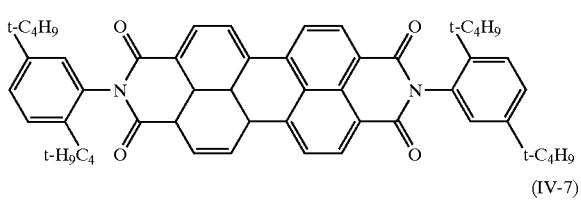
(IV-6)

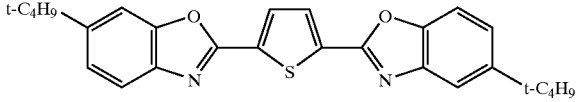
(IV-7)

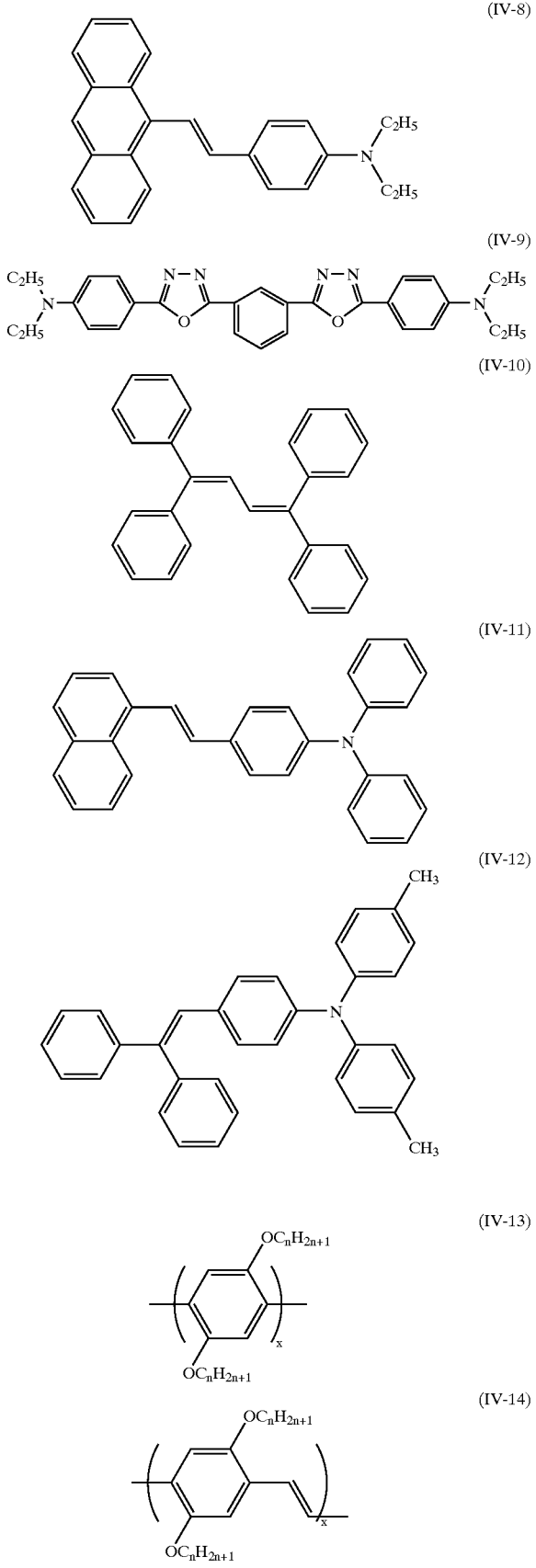

With an aim of improving the durability and the luminous efficacy of the organic light emitting diode, a dye compound different from the luminescent material may also be doped as a guest material in the luminescent material. When the emitting layer is formed by vacuum vapor deposition, doping is conducted by simultaneous vapor deposition. When the emitting layer is formed by coating and drying a solution or liquid dispersion, doping is conducted by mixing the dye into the solvent or the liquid dispersion. The ratio of the doping of the dye compound in the emitting layer is about from 0.001 to 40% by weight and, preferably, about from 0.001 to 10% by weight.

As the dye compound used for the doping, organic compounds having good compatibility with the luminescent material and not hindering the formation of favorable thin films of the luminescent material are used and, preferably, DCM derivatives, quinacridone derivatives, rubrene derivative and porphyrin are used.

Preferred specific examples of the dye compound can include the following compounds (V-1), (V-4), with no particular restriction to them.

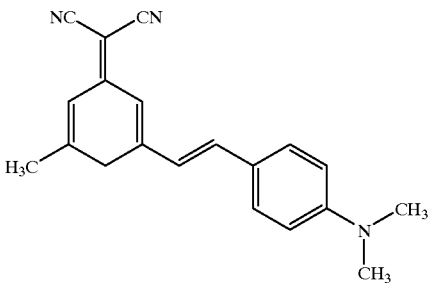
(V-1)

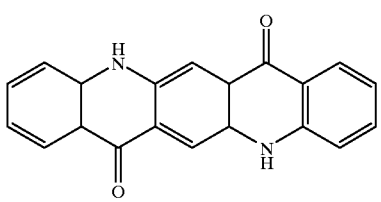
(V-2)

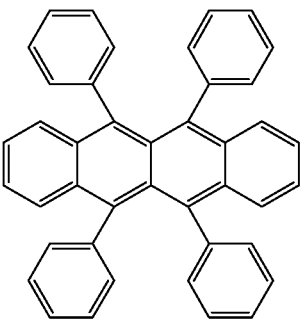
(V-3)

(V-4)

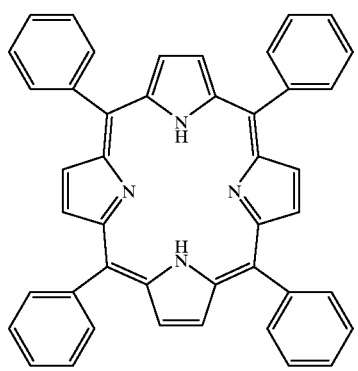

Further, when a luminescent material which can be vacuum deposited or coated and dried as a solution or a liquid dispersion but does not form a favorable thin film or does not show distinct electron transporting property is used, an electron transporting layer may be disposed between the emitting layer 4 and the back electrode 6 with an aim of improving the durability or improving the luminous efficacy of the organic electroluminescence device.

As the electron transporting material used for such electron transporting layer, those organic compounds capable of forming thin films by the vacuum vapor deposition method are preferred and oxadiazole derivatives, nitro-substituted fluolenone derivatives, diphenoquinone derivatives, thiopyran dioxide derivative and fluorenylidene methane derivative may be used. Further, an appropriate resin or additive may be added in the same manner as in the hole transporting layer. As the resin used herein, those exemplified above for the hole transporting layer can be applied.

Preferred specific examples for the electron transporting material can include the following compounds (VI-1)-(VI-3), with no particular restriction.

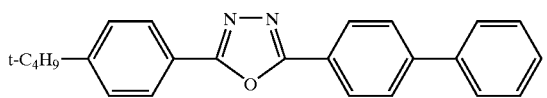
(VI-1)

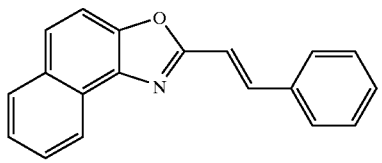
(VI-2)

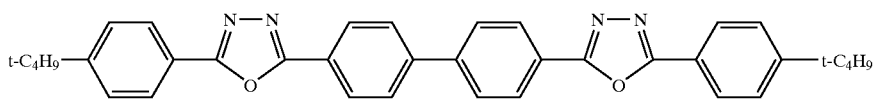
(VI-3)

In the layer constitution of the organic light emitting diode shown in FIG. 2, the emitting layer 5 having the charge transporting property is an organic compound layer formed by mixing 50% by weight or less of a luminescent material with a charge transporting polyether including repeating units containing, as partial structure, at least one kind of member selected from the structures represented by the general formulae (I-1) and (I-2), and the compounds (IV-1)-(IV-15) are suitably used for the luminescent material. Further, 1 to 50% by weight of the electron transporting material may be dispersed for controlling the balance between the holes and electrons injected in the organic light emitting diode, or an electron transporting layer including the electron transporting material may be interposed between the emitting layer 5 having the charge transporting property and the back electrode 6. As the electron transporting material described above, an organic compound showing no intense interelectron effect with the charge transporting polyether including a repeating unit, as a partial structure, at least one kind of member selected from the structures represented by the general formula (I-1) and (I-2) is used and the following compound (VII) is preferably used, with no particular restriction. In the same manner, a tetraphenylene diamine derivative may be used in an appropriate amount being dispersed simultaneously for controlling the charge mobility. Further, like the hole transporting layer in FIG. 1, an appropriate resin or additive may be added. As the resin used herein, those exemplified for the hole transporting layer can be applied. Further, a dye compound different from the luminescent material may also be doped.

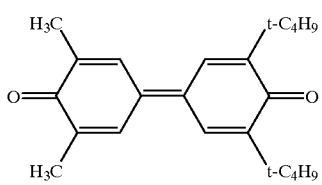
(VII)

As the back electrode 6 in FIG. 1 and FIG. 2, metals capable of vacuum vapor deposition and having a small work function for electron injection are used and, magnesium, aluminum, silver, indium and alloys thereof are particularly preferred.

In the organic light emitting diode according to this invention described above, the hole transporting layer 3 is formed by using a charge transporting polyether including repeating units, containing, as a partial structure, at least one member selected from the structures represented by the general formulae (I-1) and (I-2) and, optionally, an electron transporting material and a hole transporting material, the emitting layer 4 is formed by using a luminescent material and, optionally, a dye compound, a charge transporting polyether, an electron transporting material and a hole transporting material, the luminescence material 5 having the charge transporting property is formed by using the charge transporting polyether, and the luminescent material and, optionally, a dye compound, an electron transporting material and a hole transporting material, by dissolving or dispersing in an appropriate organic solvent, and forming a film by using the obtained coating solution on the transparent electrode, for example, by a spin coating method, a casting method or a dipping method. The emitting layer 4 may be formed into a film also by vacuum vapor deposition in a case of not containing the charge transporting polyether.

Solvent such as metanol, ethanol, n-propanol, benzyl alcohol, acetone, methyl acetate, n-butyl acetate, chloroform, tetrahydrofuran, dioxane, dichloroethane or the like may be used. The solvent may be used alone or as a mixture of two or more of them.

The thickness of each of the hole transporting layer 3 and the emitting layer 4 is about from 0.005 to 10 $\mu$m, preferably, from 0.01 to 5 $\mu$m while depending on the material. If the layer is excessively thin, pin holes are formed to cause dark spots in the light emitting diode, whereas if the layer is excessively thick, the internal resistance increases to increase the driving voltage undesirably.

Then, on the layer containing the charge transporting polyether formed as described above, an electron transporting layer containing the transporting material can be formed by using the vacuum vapor deposition method in accordance with the layer constitution of each organic light emitting diode. Further, it may also be formed, like the hole transporting layer, by dissolving or dispersing the same in an appropriate organic solvent, for example, by a spin coating method, a casting method or a dipping method by using the resultant coating solution. In this case, the solvents exemplified for the hole transporting layer described above are applicable.

A back electrode is further formed. Further, a protective layer may be disposed for preventing degradation of the device due to moisture or oxygen. Specific materials for the protective layer can include metals such as In, Sn, Pb, Au, CU, Ag and Al, metal oxides such as MgO, $SiO_2$ and $TiO_2$ and resins such as polyethylene resin, polyurea resin and polyimide resin. For forming the protective layer, a vacuum vapor deposition method, a sputtering method, a plasma polymerization method, a CVD method or a coating method can be applied.

With the procedures described above, the organic light emitting diode can be manufactured easily. The thickness for each of the emitting layer having the electron transporting property and the electron transporting layer to be laminated is within a range from 10 $\mu$m or less, preferably, 0.005 to 5 $\mu$m. If the layer is excessively thin, pin holes are formed to cause dark spots in the device, whereas if the layer is excessively thick, internal resistance increases to increase the driving voltage undesirably.

The organic light emitting diode according to this invention can emit light by applying a DC voltage, for example, of 4 to 20 V and at a current density of 1 to 200 mA/cm$^2$ between the pair of electrodes.

EXAMPLE

Examples of this invention are to be explained below but the invention is not restructured to such examples.

Example 1

An organic light emitting diode identical with the constitution shown in FIG. 1 was manufactured.

At first, after supersonically cleaning an ITO glass substrate etched to a rectangular shape of 2 mm width (transparent insulative substrate 1 having a transparent electrode 2 formed thereon) with isopropanol (for use in electronic industry, manufactured by Kanto Chemical), it was dried by a spin coater.

A hole transporting layer 3 and an emitting layer 4 were formed in this order as an organic compound layer on the substrate. That is, as the hole transporting layer 3, the charge transporting polyether represented by the general formula (II) [(exemplified compound (12)] was prepared as a 5 wt % solution in dichloroethane, which was filtered through a PTFE filter of 0.1 $\mu$m and then formed into a thin film of 0.050 $\mu$m thickness by a dipping method. Further, as the emitting layer 4, the exemplified layer (IV-1) as the luminescent material was vapor deposited to prepare a thin film of 0.065 $\mu$m thickness.

Successively, an Mg—Ag alloy was vapor deposited by simultaneous vapor deposition to prepare a back electrode 6 of 2 mm width and 0.15 $\mu$m thickness so as to intersect the ITO electrode. The effective area of the manufactured organic light emitting diode was 0.04 cm$^2$.

Example 2

An organic light emitting diode identical with the constitution shown in FIG. 2 was manufactured.

One part by weight of the charge transporting polyether used in Example 1 [exemplified compound (12)], 4 parts by weight of poly(N-vinyl carbazole) and 0.1 parts by weight of the exemplified compound (IV-1) as the luminescent material were prepared so as to form a 10 wt % solution in dichloroethane and filtered through a PTFE filter of 0.1 $\mu$m. By using the solution, a thin film of about 0.15 $\mu$m thickness was formed by a spin coating method on a glass substrate having a rectangular ITO electrode of 2 mm formed by etching thereon (transparent insulative substrate 1 having a transparent electrode 2 formed thereon), to form an emitting layer 5 having charge transporting property (organic compound layer). After drying thoroughly, an Mg—Ag alloy was vapor deposited by simultaneous vapor deposition to form a back electrode 6 of 2 mm width and 0.15 $\mu$m thickness so as to intersect the ITO electrode. The effective area of the manufactured organic light emitting diode was 0.04 cm$^2$.

Example 3

In the same manner as in Example 1, a thin film of 0.050 $\mu$m thickness was prepared from the charge transporting polyether [exemplified compound (12)] represented by the general formula (II) as the hole transporting layer (organic compound layer) on an etched and cleaned ITO glass substrate. Then, as the emitting layer (organic compound layer), a thin film of 0.065 $\mu$m thickness was formed by vapor deposition of the exemplified compound (IV-1). Further, as the electron transporting layer (organic compound layer), the exemplified compound (VI-1) as the electron transporting material was formed by simultaneous vapor deposition to a thickness of 0.030 $\mu$m. Successively, an Mg—Ag alloy was vapor deposited by simultaneous vapor deposition to form a back electrode of 2 mm width and 0.15 $\mu$m thickness so as to intersect the ITO electrode. The effective area of the manufactured organic light emitting diode was 0.04 cm$^2$.

Example 4

An organic light emitting diode was manufactured in the same manner as in Example 1 except for using the charge transporting polyether [exemplified compound (17)] represented by the general formula (II) instead of the charge transporting polyether [exemplified compound (12)] represented by the general formula II in Example 1.

Example 5

An organic light emitting diode was manufactured in the same manner as in Example 2 except for using the charge transporting polyether [exemplified compound (17)] represented by the general formula (II) instead of the charge transporting polyether [exemplified compound (12)] represented by the general formula (II) in Example 2.

Example 6

An organic light emitting diode was manufactured in the same manner as in Example 1 except for using the charge transporting polyether [exemplified compound (18)] represented by the general formula (II) instead of the charge transporting polyether [exemplified compound (12)] represented by the general formula (II) in Example 1.

Example 7

An organic light emitting diode was manufactured in the same manner as in Example 1 except for using the charge transporting polyether [exemplified compound (14)] represented by the general formula (II) instead of the charge transporting polyether [exemplified compound (12)] represented by the general formula (II) in Example 1.

Comparative Example 1

An organic light emitting diode was manufactured in the same manner as in Example 1 except for using a charge transporting compound represented by the following structural formula (VIII) instead of the compound [(exemplified compound (12))] represented by the general formula (II) in Example 1.

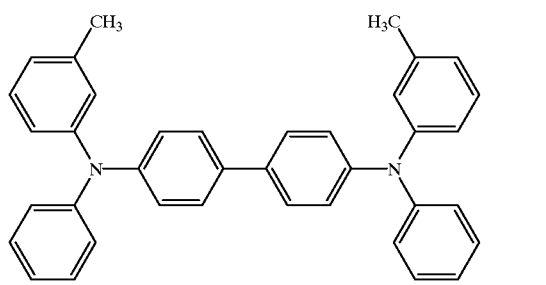

(VIII)

Comparative Example 2

2 parts by weight of polyvinyl carbazole (PVK) as a charge transporting polymer, 0.1 parts by weight of the exemplified compound (V-1) as the dye compound and 1 part by weight of the exemplified compound (VI-1) as the electron transporting material were mixed to prepare a 10 wt % solution in dichloroethane and filtered through a PTFE filter of 0.1 $\mu$m. A hole transporting layer (organic compound layer) of about 0.15 $\mu$m thickness was formed by a dipping method using the solution on a glass substrate having a rectangular ITO electrode of 2 mm width formed thereon by etching. After drying thoroughly, an Mg—Ag alloy was vapor deposited by simultaneous deposition to form a back electrode of 2 mm width and 0.15 $\mu$m thickness so as to intersect the ITO electrode. The effective area of the manufactured organic light emitting diode was 0.04 $cm^2$.

(Evaluation)

The organic light emitting diode thus manufactured was applied with a DC voltage in vacuum (0.133 Pa) with the ITO electrode as a positive side (anode) and the Mg—Ag back electrode as the negative side (cathode), light emission was measured and the maximum brightness and the luminance color were evaluated. The results are show in the following Table 4. The light emission life of the organic light emitting diode was measured in a dry nitrogen. In the evaluation for the light emission life, the current value was set such that the initial brightness was 50 $cd/m^2$ and the time of period during which the brightness was decayed to one-half of the initial value at the constant current driving was defined as the device life time (hour). The driving current density in this case is shown together with the device lifetime in the following Table 4.

TABLE 4

| | Maximum brightness ($cd/m^2$) | Luminance color | ($mA/cm^2$) | (hour) |
|---|---|---|---|---|
| Example 1 | 1110 | green | 8.5 | 30 |
| Example 2 | 1240 | green | 7.3 | 32 |
| Example 3 | 980 | green | 9.9 | 23 |
| Example 4 | 1120 | green | 6.7 | 24 |
| Example 5 | 880 | green | 8.2 | 32 |
| Example 6 | 1340 | green | 8.5 | 28 |
| Example 7 | 760 | green | 8.8 | 19 |
| Comp. Example 1 | 480 | green | 9.5 | 18 |
| Comp. Example 2 | 450 | red | 9.8 | 15 |

From the results of Table 4, it can be seen that the organic light emitting diode of this invention in Examples 1 to 7 using the charge transporting polyethers including repeating units containing, as a partial structure, at least one member selected from the structures represented by the general formulae (I-1) and (I-2) show high brightness and have long device life time.

This invention can provide an organic light emitting diode having high luminous intensity, providing stabilized performance even during repetitive use and easy to manufacture, by using a charge transporting polymer excellent in the stability upon light emission, storage stability, solubility and compatibility. Further, according to this invention, area can be enlarged easily and a favorable thin film can be formed with less failure such as pin holes by using a spin coating method or a dipping method and provides advantage also in view of the manufacturing cost.

The entire disclosure of Japanese Patent Application No. 2000-256801 filed on Aug. 28, 2000 including specification, claims, drawings and abstract is incorporated herein by reference in its entirety.

What is claimed is:

1. An organic light emitting diode having one or more organic compound layers put between a pair of electrodes, the organic light emitting diode, comprising: an anode and a cathode at least one of which is transparent or semitransparent, wherein at least one of the organic compound layers contains charge transporting polyethers comprising a repeating unit containing, as a partial structure, at least one member selected from the group consisting of structures represented by the following general formulae (I-1) and (I-2):

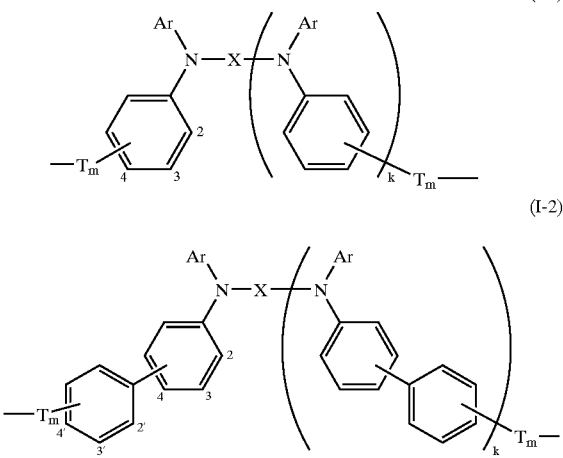

where Ar represents a substituted or non-substituted monovalent polynuclear aromatic ring having a number of aromatic rings of from 3 to 10, or a substituted or non-substituted monovalent condensed aromatic ring having a number of aromatic rings of from 2 to 10, X represents a substituted or non-substituted bivalent aromatic group, T represents a bivalent linear hydrocarbon group of 1 to 6 carbon atoms or a bivalent branched hydrocarbon group of 2 to 10 carbon atoms, m represents an integer of 1 to 3 and k represents 0 or 1.

2. The organic light emitting diode according to claim 1, comprising, as the organic compound layer on a transparent electrode in this order: a hole transporting layer containing one or more charge transporting polyethers comprising repeating units containing, as a partial structure, at least one member selected from the structures represented by the general formulae (I-1) and (I-2), and an emitting layer.

3. The organic light emitting diode according to claim 1, wherein the organic compound layer is a single layer.

4. The organic light emitting diode according to claim 1, wherein the charge transporting polyether is a polyether represented by the general formula (II):

$$R-O\text{-}[A-O]_p R \quad (II)$$

where A represents at least one member of the structures represented by the general formulae (I-1) and (I-2), R represents a hydrogen atom, an alkyl group, a substituted or non-substituted aryl group or a substituted or non-substituted aralkyl group and p represents an integer from 5 to 5000.

5. An organic light emitting diode having one or more organic compound layers put between a pair of electrodes, the organic light emitting diode, comprising: an anode and a cathode at least one of which is transparent or semitransparent, wherein at least one of the organic compound layers contains charge transporting polyethers comprising a repeating unit containing, as a partial structure, at least one member selected from the group consisting of structures represented by the following general formulae:

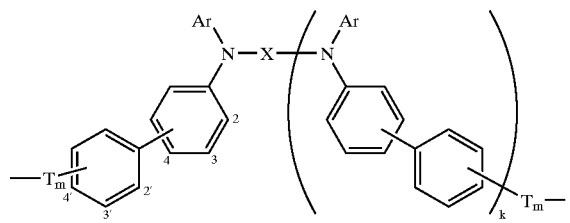

where Ar represents a substituted or non-substituted monovalent polynuclear aromatic ring having a number of aromatic rings of from 3 to 10, or a substituted or non-substituted monovalent condensed aromatic ring having a number of aromatic rings of from 2 to 10, X represents a substituted or non-substituted bivalent aromatic group, T represents a bivalent linear hydrocarbon group of 1 to 6 carbon atoms or a bivalent branched hydrocarbon group of 2 to 10 carbon atoms, m represents an integer of 1 to 3 and k represents 0 or 1.

* * * * *